(12) United States Patent
Gerber (10) Patent No.: US 8,761,888 B2
(45) Date of Patent: *Jun. 24, 2014

(54) TRANSMEMBRANE SENSING DEVICE FOR SENSING BLADDER CONDITION

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/086,016

(22) Filed: Apr. 13, 2011

(65) Prior Publication Data

US 2011/0190844 A1    Aug. 4, 2011

Related U.S. Application Data (60) Continuation of application No. 12/795,336, filed on Jun. 7, 2010, now Pat. No. 7,930,034, which is a division of application No. 11/193,310, filed on Jul. 29, 2005, now Pat. No. 7,769,460.

(51) Int. Cl.
*A61N 1/00* (2006.01)

(52) U.S. Cl.
USPC .......................................................... 607/41

(58) Field of Classification Search
USPC ..................................................... 607/40, 41
See application file for complete search history.

(56) References Cited

U.S. PATENT DOCUMENTS

| | | | |
|---|---|---|---|
| 4,739,764 A | 4/1988 | Lue et al. | |
| 5,103,835 A | 4/1992 | Yamada et al. | |
| 6,354,991 B1 | 3/2002 | Gross et al. | |
| 6,360,123 B1 | 3/2002 | Kimchi et al. | |
| 6,393,323 B1 | 5/2002 | Sawan et al. | |
| 6,652,449 B1 | 11/2003 | Gross et al. | |
| 6,689,056 B1 | 2/2004 | Kilcoyne et al. | |
| 6,695,885 B2 | 2/2004 | Schulman et al. | |
| 6,805,667 B2 | 10/2004 | Christopherson et al. | |
| 7,610,093 B2 | 10/2009 | Gerber et al. | |
| 7,769,460 B2 | 8/2010 | Gerber | |
| 7,930,034 B2 * | 4/2011 | Gerber ........................... | 607/41 |
| 2001/0001125 A1 | 5/2001 | Schulman et al. | |
| 2002/0062060 A1* | 5/2002 | Gross et al. ..................... | 600/30 |
| 2002/0072780 A1* | 6/2002 | Foley ............................... | 607/40 |

(Continued)

OTHER PUBLICATIONS

Coosemans et al., "Datalogger for Bladder Pressure Monitoring with Wireless Power and Data Transmission", Katholieke Universiteit Leuven, Department ESAT-MICAS, Belgium, Oct. 17, 2003, (1 page).

(Continued)

*Primary Examiner* — Christopher D Koharski
*Assistant Examiner* — Roland Dinga
(74) *Attorney, Agent, or Firm* — Shumaker & Sieffert, P.A.

(57) ABSTRACT

The disclosure describes a sensing device that is implantable to sense bladder conditions, as well as a neurostimulation system and method that make use of such a sensor for alleviation of urinary incontinence. The sensing device is implantable outside the bladder, but includes a lead that penetrates the bladder wall to deploy a sensor within the bladder. Using the sensor on the lead, the sensing device outside the bladder is able to detect a condition within the interior of the bladder. In this sense, the sensing device provides transmembrane sensing of internal bladder conditions. The condition may be indicative of bladder filling or bladder contraction, and may be used to control electrical stimulation applied to the patient to alleviate urinary incontinence.

18 Claims, 8 Drawing Sheets

(56) References Cited

U.S. PATENT DOCUMENTS

| | | |
|---|---|---|
| 2002/0103424 A1 | 8/2002 | Swoyer et al. |
| 2002/0193840 A1 | 12/2002 | Sawan et al. |
| 2003/0100930 A1 | 5/2003 | Cohen et al. |
| 2003/0144708 A1* | 7/2003 | Starkebaum .................. 607/40 |
| 2005/0149142 A1* | 7/2005 | Starkebaum .................. 607/40 |
| 2005/0192635 A1* | 9/2005 | Creasey et al. .................. 607/2 |
| 2005/0245840 A1* | 11/2005 | Christopherson et al. .... 600/561 |
| 2006/0020225 A1* | 1/2006 | Gerber et al. ................ 600/561 |
| 2006/0190050 A1* | 8/2006 | Gerber et al. ................ 607/41 |
| 2006/0247724 A1* | 11/2006 | Gerber et al. ................ 607/41 |
| 2006/0247725 A1* | 11/2006 | Gerber et al. ................ 607/41 |

OTHER PUBLICATIONS

Siwapornsathain et al., "A Telemetry and Sensor Platform for Ambulatory Urodynamics", Department of Electrical and Computer Engineering, University of Wisconsin, Madison, WI, 2002, (5 pages).

Van Waalwijk van Doorn et al., "Standardisation of Ambulatory Urodynamic Monitoring", Report of the Standarisation Sub-committee of the ICS ambulatory urodynamic studies, 2000, (21 pages).

"Wireless Physiological Pressure Transducer", MEMSCAP Sensor Solutions, May 2003, (2 pages).

* cited by examiner

TRANSMEMBRANE SENSING DEVICE FOR SENSING BLADDER CONDITION

This application is a continuation of application Ser. No. 12/795,336, filed Jun. 7, 2010, which is a divisional of application Ser. No. 11/193,310, filed Jul. 29, 2005. The entire contents of these applications are incorporated by reference.

TECHNICAL FIELD

The invention relates to implantable medical devices and, more particularly, implantable sensors.

BACKGROUND

Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients also may suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence.

Monitoring the current state of the bladder may enable a physician to track the disease or even determine the best mode treatment. Electrical stimulation of nerves in the pelvic floor may provide an effective therapy for a variety of disorders, including urinary incontinence. For example, an implantable neurostimulator may be provided to deliver electrical stimulation to the sacral nerve to induce sphincter constriction and thereby close or maintain closure of the urethra at the bladder neck. In addition, electrical stimulation of the bladder wall may assist fluid retention in the bladder or voiding fluid from the bladder. An appropriate course of neurostimulation therapy may be aided by a sensor that monitors physiological conditions of the bladder. In some cases, an implantable stimulation device may deliver stimulation therapy based on the level or state of a sensed physiological condition.

SUMMARY

The disclosure is directed to a sensing device that is implantable to sense bladder conditions, as well as a neurostimulation system and method that make use of such a sensor for alleviation of urinary incontinence. The sensing device is implantable outside the bladder, but includes a lead that penetrates the bladder wall to a sensor deployed within the bladder. Using the sensor on the lead, the sensing device outside the bladder is able to detect a condition within the interior of the bladder. In this sense, the sensing device provides transmembrane sensing of internal bladder conditions. The internal bladder condition may be indicative of bladder filling, expansion or contraction, or pH, and may be used to control electrical neurostimulation applied to the patient to alleviate urinary incontinence.

Inadequate urinary sphincter force, insufficient pelvic floor muscle tone, other pelvic floor disorders, or neurological conditions may result in involuntary bladder voiding, i.e., urinary incontinence. The sensing device may provide short- or long-term monitoring of bladder conditions, e.g., for analysis by a clinician in diagnosing bladder disorders. Alternatively, the sensing device may form part of a closed-loop neurostimulation system. For example, neurostimulation therapy can be responsive to the sensing device to activate or adjust stimulation based on sensed bladder conditions. If sensed bladder conditions indicate that involuntary voiding is possible, e.g., due to bladder contraction or bladder filling, the neurostimulator may apply stimulation pulses to increase sphincter pressure, enhance pelvic floor muscle tone, or both, and thereby prevent or stop involuntary urine leakage when voiding is not desired by the patient, thus alleviating urinary incontinence.

In one embodiment, the invention provides a method comprising sensing a bladder condition via an implanted sensor disposed within the bladder and deployed by a lead, and providing the sensed bladder condition to a device disposed outside of the bladder via the lead.

In another embodiment, the invention provides an implantable electrical stimulation system comprising a sensing device, a lead extending from the sensing device for introduction into an interior of a bladder, a sensor, carried at a distal end of the lead, that senses a condition within the interior of the bladder, a processor within the sensing device that generates information based on the sensed bladder activity, and an implantable stimulator that delivers stimulation therapy based on the information.

In various embodiments, the invention may provide one or more advantages. For example, measuring bladder activity with a small sensor deployed inside the bladder may provide an accurate measurement of bladder characteristics such as bladder pressure. However, sensor processing electronics, telemetry circuitry and a power source may be implanted outside the bladder, permitting larger size without impeding or obstructing internal bladder function. For example, a larger battery may be provided in the sensing device positioned outside the bladder. In addition, in some embodiments, the transmembrane lead and sensor may be coupled to an integrated neurostimulation and sensing device. With closed-loop stimulation, a stimulator may generate stimulation parameter adjustments, based on the sensed conditions, to more effectively target the function of the urinary sphincter muscle or pelvic floor muscle tone, thereby enhancing stimulation efficacy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
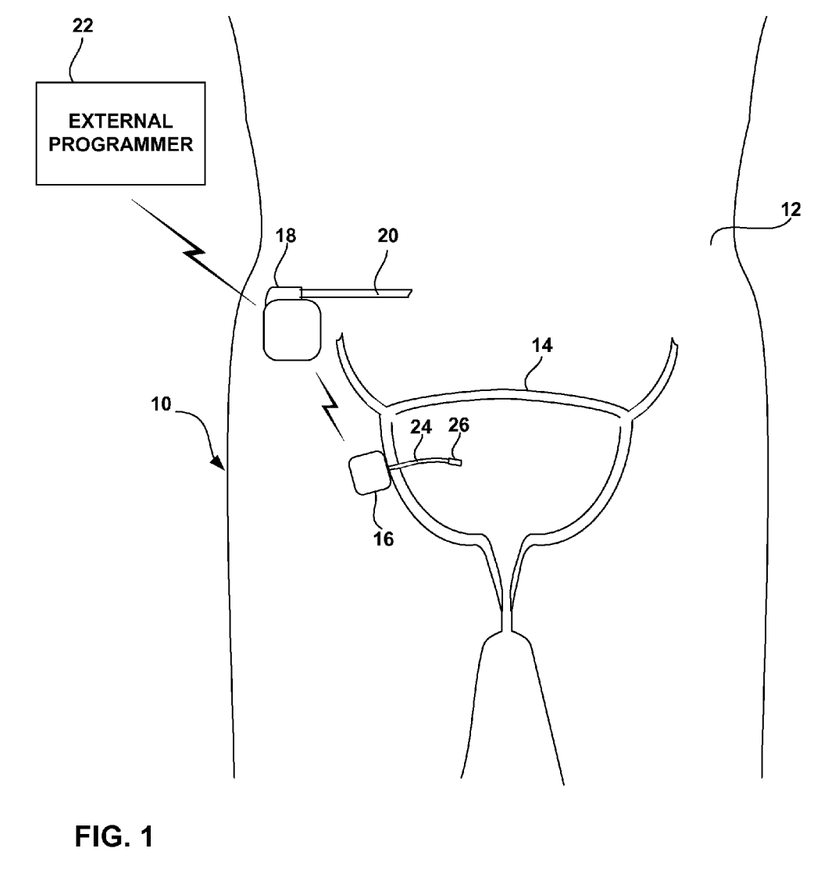
FIG. 1 is a schematic diagram illustrating an implantable stimulation system, incorporating an implantable sensing device in communication with an implantable stimulator, for treating urinary incontinence.

FIG. 1 is a schematic diagram illustrating an implantable stimulation system 10, incorporating an implantable sensing device 16 in communication with an implantable stimulator 18, for treating urinary incontinence. As shown in FIG. 1, system 10 may include an implantable sensing device 16, implantable stimulator 18 and external programmer 22, shown in conjunction with a patient 12. Sensing device 16 is located external to bladder 14 and senses changes in bladder conditions, such as fill level, expansion or contraction. In some embodiments, sensing device 16 also may monitor other bladder conditions, such as urine pH, e.g., as an indication of bladder infections. Bladder conditions are sensed by sensing device 16 using an internal bladder sensor 26 coupled to the sensing device via a sensing lead 24. Bladder conditions may be sensed using any of a variety of sensors, such as sensors that measure impedance, pH, pressure, distance or other parameters. For example, a pressure sensor may indicate a fill stage or contraction. As another example, sensing device 16 may detect the distance across the inside of bladder 14 with an ultrasound transducer to generate information regarding the size of bladder 14. As another alternative, sensing device 16 may sense an amount of urine in bladder 14 using an impedance sensor.

Sensing lead 24 penetrates a wall of bladder 14. Sensor 26 is mounted at a distal end of sensing lead 24. Sensing lead 24 couples sensor 26 and sensing device 16 by tunneling through the wall of bladder 14. Sensing device 16 transmits information based on conditions sensed by sensor 26 to at least one of stimulator 18 and external programmer 22 by wireless telemetry. In some embodiments, sensing device 16 may transmit information to stimulator 18 by a wired connection. In other embodiments, sensing device 16 may be structurally integrated with stimulator 18. Stimulator 18 or programmer 22 may record the information, generate adjustments to electrical stimulation parameters applied by the stimulator, or both. In some embodiments, sensing device 16 may support purely diagnostic purposes, such as urodynamic study, e.g., by transmission of information to external programmer 22. In other embodiments, sensing device 16 may form part of a closed loop feedback system for stimulator 18.

Implantable stimulator 18 is coupled to lead 20, which is tunneled through patient 12 to one or more nerve sites. Lead 20 contains one or more electrodes at the distal end to transfer electrical stimulation pulses from stimulator 18 to nerves which innervate the urinary system. Lead 20 may terminate at nerves in the pelvic floor, such as the sacral nerve or pudendal nerve. Sacral nerve stimulation, for example, may improve pelvic floor muscle tone or result in contraction of the urinary sphincter which keeps urine inside bladder 14. Appropriate nerve stimulation may assist patient 12 in avoiding urinary incontinence or promoting the elimination of urine from bladder 14. As an exemplary embodiment, stimulation of the sacral nerve to improve pelvic floor muscle tone or urinary sphincter function will be used herein. However, many other nerves, sphincters or muscles may be stimulated to treat urinary disorders such as urinary incontinence.

Figure 2:
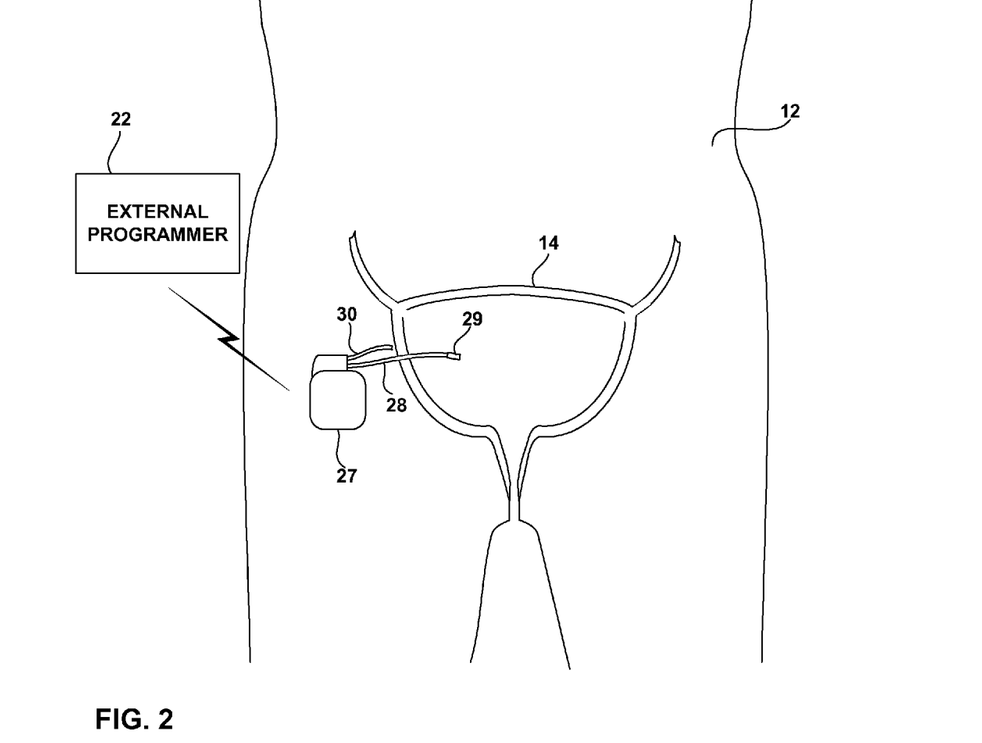
FIG. 2 is a schematic diagram illustrating an implantable stimulation system, incorporating an implantable stimulator electrically coupled to a sensing device, for treating urinary incontinence.

FIG. 2 is a schematic diagram illustrating an implantable stimulation system, incorporating an implantable stimulator electrically coupled to a sensing device, for treating urinary incontinence. As shown in FIG. 2, implantable stimulator 27 is coupled to both a sensing lead 28 and a stimulation lead 30 (partially shown in FIG. 2). Stimulation lead 30 may carry one or more stimulation electrodes for delivery of stimulation pulses. A sensor 29 is formed at the distal end of sensing lead 28. An external programmer 22 communicates with stimulator 27 by wireless telemetry. Similar to FIG. 1, bladder activity is sensed and used to activate or adjust stimulation therapy. However, stimulator 27 integrates electronics and other components to support both sensing of bladder activity and delivery of stimulation. Sensor 29 may be configured, as described above with respect to FIG. 1, to sense any of a variety of parameters such as impedance, pH, pressure or bladder size within bladder 14. The sensed parameters may be used to determine bladder size or pressure, which correlate with a bladder fill stage or contractile event or state. Integration of sensor 29 and lead 28 with stimulator 27 permits closed-loop feedback information without the need for communication between two separate devices.

Figure 3:
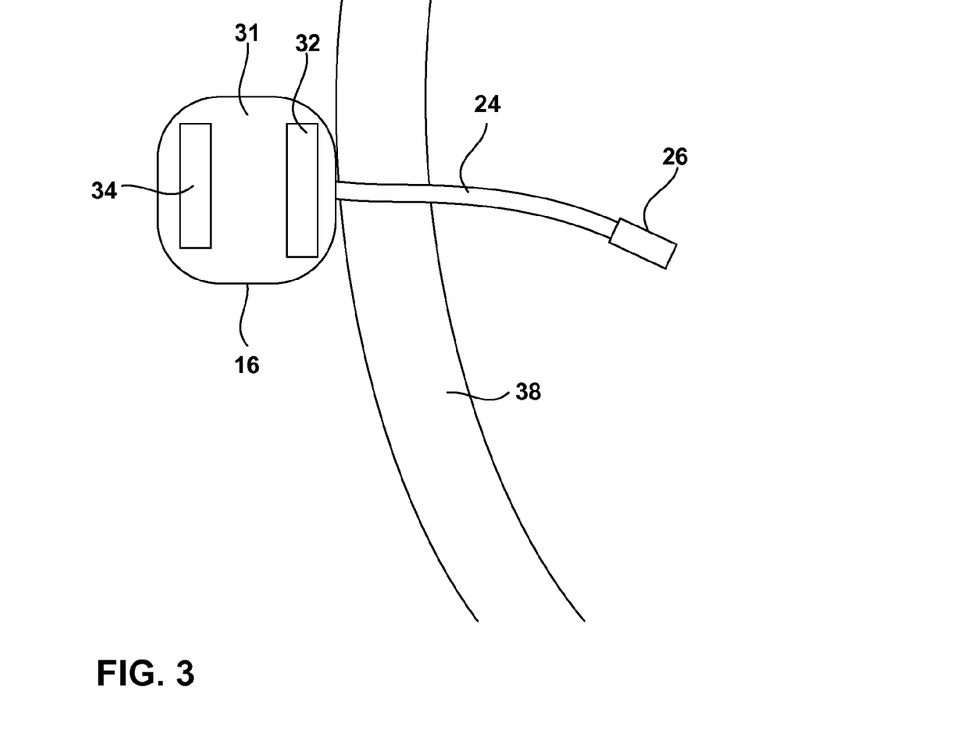
FIG. 3 is a cross-sectional illustration of an implantable sensing device within a bladder of a patient connected to a device outside of the bladder by a lead.

FIG. 3 is a cross-sectional illustration of an implantable sensing device within a bladder of a patient connected to a device outside of the bladder by a lead. As shown in FIG. 3, sensing device 16 includes a device housing 31 and sensing lead 24 that extends from the housing through bladder wall 38 and into bladder 14. The distal end of sensing lead 24 carries sensor 26. Device housing 31 includes a circuit board 32 carrying sensing circuitry which is electronically coupled to sensor 26, as well as a power source 34.

Power source 34 may take the form of a small rechargeable or non-rechargeable battery, which may be configured as a coin cell or pin cell. However, use of a sensing device 16 that resides outside of bladder 14 may permit the use of a larger battery. Different types of batteries or different battery sizes may be used, depending on the requirements of a given application. To promote longevity, power source 34 may be rechargeable via induction or ultrasonic energy transmission, and includes an appropriate circuit for recovering transcutaneously received energy. For example, power source 34 may include a secondary coil and a rectifier circuit for inductive energy transfer. Power generation or charging electronics may be carried on circuit board 32. In still other embodiments, power source 34 may not include any storage element, and sensing device 16 may be fully powered via transcutaneous inductive energy transfer. As a further alternative, stimulator 18 or programmer 22 may be configured to apply inductive power to sensing device 16 whenever sensing is desired. In this case, when inductive power is not applied, sensing device 16 is asleep. Upon application of inductive power, sensing device 16 wakes up, acquires a sense signal, and transmits the signal to programmer 22 or stimulator 18. Accordingly, stimulator 18 or programmer 22 determines the sampling rate of sensor 16 by powering up the sensor at desired intervals.

Circuit board 32 includes processing electronics to process signals generated by sensing element 26, and generate bladder condition information based on the signals. In addition, circuit board 32 includes telemetry circuitry for wireless telemetry with stimulator 18, external programmer 22, or both. Sensing device 16 rests near the external surface of bladder wall 38. In some embodiments, device housing 31 may be attached to bladder wall 38 by any of a variety of mechanical fixation devices, such as helical screws, sutures, or barbed hooks, as well as surgical adhesives. Alternatively, sensing device 16 may be fixed to tissue within the pelvic or abdominal region of patient 12.

While housing 31 is located external to bladder 14, measurements of bladder activity are taken within the bladder by sensor 26. Transmembrane implantation of lead 24 allows sensor 26 to detect changes within bladder 14 while completely sealing the wall 38 of the bladder after implantation. The hole formed in bladder wall 38 may be sized sufficiently small to ensure that lead 24 substantially seals the hole. For example, lead 24 and sensor 26 may have maximum outer diameters in a range of approximately 0.5 to 5 mm. In addition, surgical adhesive may be provided around the junction between lead 24 and bladder wall 38 to enhance sealing. In some embodiments, sensing device 16 may couple to more than one lead 24 to provide multiple sensing points within bladder 14.

Sensor housing 31 may be made from a biocompatible material such as titanium, stainless steel or nitinol, or a polymeric material such as silicone or polyurethane. Another material for fabrication of sensor housing 31 is a two-part epoxy. An example of a suitable epoxy is a two-part medical implant epoxy manufactured by Epoxy Technology, Inc., mixed in a ratio of 10 grams of resin to one gram of activator. In general, sensor housing 31 contains no external openings, with the exception of the opening containing lead 24, thereby protecting circuit board 32 and power source from the environment within the abdominal cavity of patient 12. The opening in sensor housing 31 that receives lead 24 is sealed to prevent exposure of interior components.

Circuit board 32 controls the operation of sensing device 16 and receives an output signal from sensing element 26. Sensing element 34 contains the electronics for controlling sensor 26 within bladder 14. For example, sensing element 34 regulates the current and voltage of input signal sent to sensor 26 in order to detect bladder activity. The signal generated by sensor 26 is measured and amplified by processing electronics on circuit board 32 to create the output signal. The processing electronics on circuit board 32 may convert the signal generated by sensor 26 to a digital signal and process the signal to create bladder condition information.

Sensing device 16 transmits the bladder condition information by wireless telemetry directly to external programmer 22, stimulator 18, or both. The bladder condition information may indicate that a urine voiding event is imminent, e.g., based on a fill level of bladder 14, urine pressure within the bladder, or bladder size or volume. Stimulator 18 may activate or adjust stimulation to prevent involuntary urine leakage. Stimulation may be increased or decreased by adjusting one or more stimulation parameters such as amplitude (current or voltage), pulse width or pulse rate. Adjustment also may include selection of different electrodes or polarities. At the same time, external programmer 22 may signal patient 12 that bladder 14 should be voided based on the bladder condition information. Once stimulator 18 receives confirmation from patient 12 to void bladder 14, the stimulator may temporarily cease stimulation to allow urine to exit bladder 14. Sensing device 16 may monitor the state of bladder 14 to signal the end of voiding and the beginning of renewed stimulation. In other embodiments, patient 12 may signal stimulator 18 through external programmer 22 that voiding has completed. This signal may allow stimulator 18 to restart simulation if necessary. Wireless communication between sensing device 16 and stimulator 18 is not necessary as the components of both devices are housing within the stimulator.

For spinal cord injury patients who cannot perceive a sensation of bladder fullness or other sensation, sensing device 16 may be utilized with or without implantable stimulator 18. Sensing device 16 may communicate the condition of bladder 14 to external programmer 22, which signals patient 12 as to the status of the bladder. External programmer 22 may contain an LCD, LED lights, other display, audio feedback or tactile feedback. The feedback may inform patient 12 or the state of bladder 14 or if it is time to urinate to avoid an incontinence event. If voiding is needed, the patient may self-catheterize to relieve the contents of bladder 14. Moreover, patient 12 may utilize system 10 for planning the ingestion of solid or liquid food. For example, if bladder 14 is becoming full and bladder voiding is not possible shortly, patient 12 may stop any drinking or eating activities to help avoid an incontinence event or avoid a dangerously high bladder pressure that could result in kidney problems.

In addition, stimulator 18 may adjust stimulation parameters in response to bladder condition information transmitted by implantable sensing device 16. Programmer 22 or implantable stimulator 18 may adjust stimulation parameters, such as amplitude, pulse width, and pulse rate, electrode combination or polarity, based on bladder information received from implantable sensor 16. In this manner, implantable stimulator 18 adjusts stimulation to either increase or reduce urinary sphincter contraction or enhance pelvic floor tone based on the actual bladder state or trend in changes. Sensing device 16 may transmit bladder information periodically, e.g., every few seconds or minutes. In some embodiments, sensing device 16 may transmit bladder information when there is an abrupt change sensed by sensing element 26, such as a pressure or volume change that exceeds a predetermined threshold. Alternatively, or additionally, adjustment may involve on and off cycling of the stimulation in response to bladder size indicative of a particular bladder fill stage. For example, stimulation may be turned off until the bladder size exceeds a threshold indicative of a particular fill stage of the bladder, at which time stimulation is turned on. Stimulation parameters may be further adjusted as the sensed bladder size continues to increase, so that involuntary leakage can be prevented. Bladder condition information such as fill level or contraction may be sensed by impedance, pH, pressure, distance or volume measurements.

External programmer 22 may be a small, battery-powered, portable device that accompanies patient 12 throughout a daily routine. As mentioned previously, programmer 22 may have a simple user interface, such as a button or keypad, and a display or lights. Bladder condition information may be transmitted directly to stimulator 18 from sensing device 16 for adjustment of stimulation parameters. Alternatively, programmer 22 may receive bladder condition information from sensing device 16 and transmit command signals to stimulator 18 to adjust stimulation parameters.

Patient 12 may initiate a voiding event, i.e., a voluntary voiding of bladder 14, via the user interface provided by programmer 22. In some embodiments, the length of time for a voiding event may be determined by pressing and holding down a button for the duration of a voiding event, pressing a button a first time to initiate voiding and a second time when voiding is complete, or by a predetermined length of time permitted by programmer 22 or implantable stimulator 18. In each case, programmer 22 causes stimulator 18 to temporarily deactivate or maintain the level of stimulation so that voluntary voiding is possible.

Implantable stimulator 18 may be surgically implanted at a site in patient 12 near the pelvis. The implantation site may be a subcutaneous location in the side of the lower abdomen or the side of the lower back or upper buttocks. One or more electrical stimulation leads 20 are connected to implantable stimulator 18 and surgically or percutaneously tunneled to place one or more electrodes carried by a distal end of the lead at a desired nerve site, such as a sacral nerve site within the sacrum.

Surgical implantation of sensing device 16 may be completed by a surgeon through a number of different methods. Less invasive methods include laparoscopic implantation into the abdomen. The surgeon creates one or more small incisions into the skin near the abdomen and navigates sensing device 16 to the desired location for monitoring bladder activity. Navigation to bladder 14 is facilitated by a small video camera inserted along with device 16. The surgeon punches a small hole into bladder wall 38 and feeds lead 24 through the new hole. In some embodiments, a cystoscope may be inserted into the bladder through the urethra and used to view the introduction of sensor 26 into bladder 14. Once lead 24 is located within bladder 14, the surgeon removes the hole punching tool and bladder wall 38 seals around the surface of lead 24.

In other embodiments, more invasive techniques for implanting sensing device 16 may be used. The surgeon may open the abdominal cavity and reach bladder wall 38 by moving adjacent organs to the side. Similar to the laparoscopic technique, the surgeon may create a hole through bladder wall 38 and feed lead 24 into bladder 14. During this surgery, implantation of stimulator 18 may be completed to avoid a second operation of patient 12.

While device housing 31 does not need to be attached to bladder wall 38, it may be desirable in certain situations. Attaching implantable sensing device 16 to bladder wall 38 of bladder 14 may be accomplished in a variety of ways, but preferably is completed in a manner that will not excessively injure bladder 14 or otherwise cause excessive trauma during implantation. Preferably, attachment should cause limited inflammation and substantially no adverse physiological modification, such as tissue infection or a loss in structural integrity of bladder 14. However, it is desirable that implantable sensing device 16 also be attached securely to the attachment site in order to provide an extended period of measurement without prematurely loosening or detaching from the intended location.

Fixation of device housing 31 to bladder wall 38 may be performed for permanent or temporary attachment. For example, barbed hooks coupled to housing 31 may permanently keep housing 31 connected to bladder wall 38. Alternatively, degradable suture or pins may set housing 31 in place along bladder wall 38 to allow the hole in the bladder wall to heal around lead 24. Once bladder wall 38 has healed to secure lead 24 within the wall, the degradable suture or pins may be absorbed by patient 12 to remove fixation stress exerted on bladder 14.

In the example of FIGS. 1 and 2, sensor housing 31 of implantable sensing device 16 is attached to the exterior bladder wall 38 of bladder 14 near the side of the bladder. However, the attachment site for sensor housing 24 could be anywhere on bladder wall 38 that does not interfere with bladder function or other organ function. For example, sensor housing 24 may be placed in the top of the bladder or near the urethra. In some patients, the most desirable position may coincide with the least invasive implantation surgery.

After the useful life of implantable sensing device 16 is complete or it is no longer needed within patient 12, it can be removed from patient 12. Alternatively, sensing device 16 may simply remain implanted. As an example, using laparoscopic techniques, a recovery device may be inserted into patient 12, navigated to bladder 14, and attached to sensing device 16. The recovery device may then be withdrawn from bladder 14, explanting sensor 16 from patient 18. Alternatively, a surgeon may perform open abdominal surgery to remove the implanted sensing device 16 and stimulator 18.

Figure 4A:
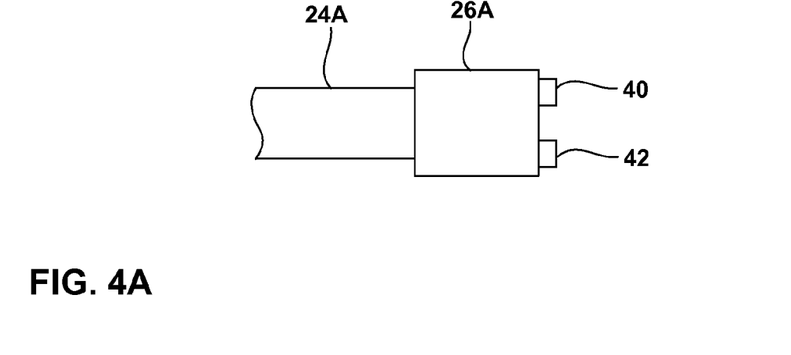
FIGS. 4A, 4B and 4C are illustrations of exemplary sensors which detect a certain bladder activity.
Figure 4B:
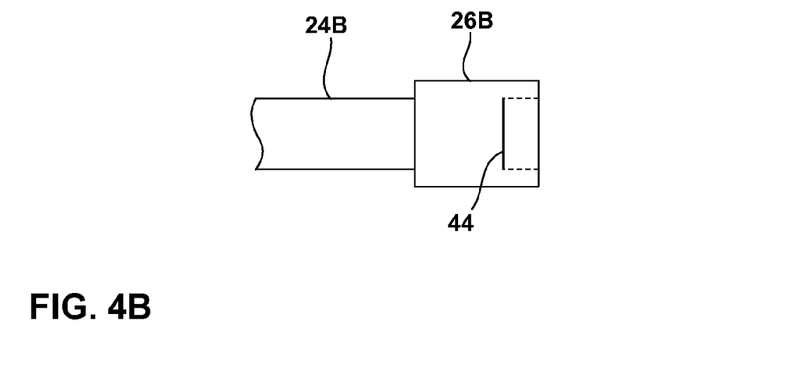
Figure 4C:
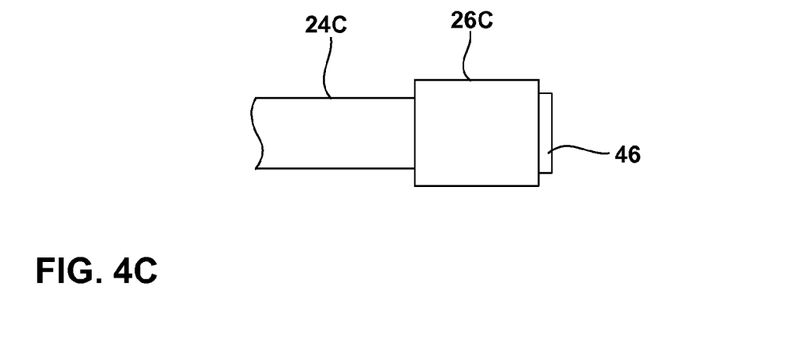

FIGS. 4A, 4B and 4C are illustrations of exemplary sensors attached to a transmembrane lead which detect a certain bladder activity. Leads 24A, 24B and 24C may be connected to sensing device 16. Sensors 26A, 26B and 26C may be used in place of sensor 26 coupled to sensing device 16 or sensor 29 coupled to stimulator 27. FIG. 4A is an exemplary embodiment of sensor 26A attached to lead 24A. Lead 24A is coupled to sensing device 16 which provides an input signal to operate sensor 26A and receives an output signal from sensor 26A representative of bladder activity.

Electrodes 40 and 42 are exposed to the contents of bladder 14 and electrically coupled to sensor 36A. Electrode 40 is an anode while electrode 42 is a cathode. Electrical current provided from electrode 40 travels through the contents of bladder 14 and arrives at cathode electrode 42. Depending on the amount of urine contained within bladder 14, the current flowing between electrodes 40 and 42 may change. Sensing element 34 may be configured to detect this change which is representative of the impedance of the urine. Some embodiments may include more or less electrodes for sensing impedance.

Impedance of the urine may provide bladder information regarding the health of the kidneys of patient 12 as well as indicate the amount of urine within bladder 14. This information may then be used as feedback to provide stimulation therapy to alleviate urinary incontinence. In some embodiments, the amount of current that passes through electrodes 40 and 42 may serve to indicate the amount of urine present in bladder 14. Based on an impedance change, sensor 16 determines when the bladder has reached a predetermined fill level. In response, sensor 16 may send a fill level condition signal to stimulator 18 to trigger activation or adjustment of electrical stimulation.

In some embodiments, electrodes 40 and 42 may terminate at bladder wall 38. Sensor 36A may detect the impedance of bladder wall 38 which could indicate the thickness of the bladder wall. As bladder 14 fills with urine, bladder wall 38 stretches and decreases in thickness. As bladder wall 38 decreases in thickness, impedance between electrodes 40 and 42 may decrease as a function of increasing bladder size. This bladder information may be used for stimulation feedback or purely monitoring purposes.

In other embodiments, electrodes 40 and 42 may be used to detect the pH of urine in bladder 14. Detecting pH may provide information regarding the health of patient 12 or the health of a specific organ. Alternatively, pH may change as urine fills bladder 14. Sensing element 34 may monitor the trends in changing pH to detect problems with bladder 14 of organs. In some embodiments, pH sensing may be applied to monitor bladder infections or other bladder disorders.

FIG. 4B illustrates an exemplary embodiment of a sensor 26B attached to lead 24B. Lead 24B is coupled to sensing device 16 which provides an input signal to operate sensor 26B and receives an output signal from sensor 26B representative of bladder condition. Sensor 26B may take the form of a pressure sensor 44, such as a strain gauge, that senses the pressure of urine within bladder 14. Other types of pressure sensors, such as piezoelectric elements, may also be used. The sensed pressure may be correlated with a bladder fill stage or a contraction. Slowly changing pressure levels may indicate a transition between different fill states, while rapid or instantaneous changes in pressure may indicate a bladder muscle contraction.

As shown in FIG. 4B, pressure sensor 44 may be recessed within sensor 26B to sense the pressure within bladder 14. A strain gauge may carry a circuit containing resistive elements, which may be printed, deposited or otherwise formed on a flexible diaphragm material. The diaphragm is in fluid contact with urine within bladder 14, and deflects as the pressure of the urine increases. For example, as fluid fills bladder 14, the strain gauge deflects inward from the increasing pressure of urine. Increases in pressure are representative of more urine in bladder 14 and are used to create bladder condition information relating to fill stage for stimulation feedback or bladder status. In this manner, pressure sensor 44 senses urine pressure, and hence bladder filling, in terms of changes in impedance, voltage, or other electrical characteristics of the circuit formed on the strain gauge. Processing electronics carried by circuit board 32, or carried by stimulator 18 or external programmer 22, process the sensed strain gauge measurements to detect a fill level or contraction of the bladder 14.

The electrical characteristics may be monitored for rapid or instantaneous changes indicative of bladder contraction, as well as slow, gradual changes indicative of bladder filling. Rapid and gradual changes may both indicate progression of the bladder toward an imminent voiding event. For example, contraction may result in an immediate leakage of urine, while bladder filling may result in an eventual leakage of urine when the bladder becomes too full. In both cases, activation or adjustment of electrical stimulation may be desirable to prevent involuntary leakage. The characteristics measured by pressure sensor 44 and processing electronics carried by circuit board 32 may be sent to stimulator 18 or programmer 32 as raw measurements or as bladder condition signals indicating a bladder condition, such as a state of fullness or a contractile condition.

Based on a sensed condition, such as bladder pressure or bladder size, sensing device 16 may sense bladder fill stage, bladder contractions, or both. Bladder fill stage may be determined based on a correlation with bladder size or pressure. Bladder size or pressure may gradually change as the bladder 14 fills with urine. However, sensing device 16 also may sense rapid, instantaneous changes in bladder size or pressure and correlate such changes with bladder contractions. Closed-loop control of stimulator 18 may proceed based on fill stage, presence of a contraction, or both.

As discussed above, the amount of bladder pressure or bladder size may correlate with a fill stage. As the fill stage increases, stimulator 18 may apply progressively greater levels of stimulation to prevent an involuntary voiding event, i.e., unintended bladder leakage. Accordingly, stimulator 18, either independently or under control of programmer 22, may adjust the stimulation level as the amount of bladder pressure or bladder size sensed by sensing device 16 indicates a particular fill stage, and may adjust the stimulation level in steps over a series of sensed fill stages. The stimulation level may be adjusted in discrete steps or in proportion to the sensed fill stage.

In addition to sensing gradually changing pressure levels or bladder size indicative of fill stage, sensing element 30 may sense rapid or instantaneously changing pressure levels or bladder size as being indicative of bladder contraction. For example, contraction of the detrusor muscle may be sensed and interpreted as a precursor to an imminent voiding event if the level of contraction exceeds a predetermined threshold level. In this case, stimulator 18 may quickly increase the stimulation level to a level intended to stop or prevent an involuntary voiding event. The stimulation level may be increased in discrete steps or in proportion to the level of the contraction. The stimulation level may be decreased gradually if contractions subside.

To sense both gradual deformation and instantaneous contractions as bladder activity or condition signals, processing circuitry within sensing device 16, or stimulator 18 or programmer 22, may apply two different processing schemes. For gradual changes, indicative of transition between fill stages, the present deformation level may be compared to a threshold level, on an absolute basis. For rapid contraction, however, the applicable threshold level may be dynamic. In particular, the threshold level for contractions may be adjusted as the gradual pressure or size level increases or decreases. In this manner, a contraction may be detected as a rapid change in pressure or size, relative to the present pressure or size level.

If the deformation level has gradually increased from a baseline to level X, then level X can be correlated with a fill stage. A rapid contraction then can be sensed by determining whether the pressure or size level rapidly increases to $X+\Delta$, where $\Delta$ represents the amount of pressure or size change associated with a detrusor muscle contraction. Hence, gradual pressure or size changes may be correlated with a fill stage on an absolute basis, whereas contraction may be determined as the delta between the steady state pressure or size level and an instantaneous change in the pressure or size level. Suitable processing electronics, including appropriate comparator, filter, and sample and hold circuitry, may be provided in sensor 16 to sense both fill stage and instantaneous muscle contractions.

As an alternative, two different sensing elements may be used to sense bladder fill stage and contraction. In this case, the contraction threshold level need not be dynamic, and may be configured to respond only to higher frequency changes. As a further alternative, in some embodiments, sensing of contractions may be correlated with a particular fill stage. If it is assumed that detrusor muscle contractions will begin to occur at a particular fill stage, for example, then sensing of contractile activity may be interpreted as a fill stage of bladder 14. Accordingly, delivery of stimulation may be adjusted in response to a fill stage as determined by absolute pressure level or size, or as a fill stage determined by the onset of bladder contractions. In either case, stimulator 18 is able to react to bladder condition or activity signals and thereby adjust stimulation levels to avoid involuntary voiding.

Increasing pressure in bladder 14 may increase the potential for urinary incontinence. As bladder 14 pressure continues to increase from addition urine, the urinary sphincter and pelvic floor muscles must provide additional force to seal the urethra of the bladder. If the urinary sphincter or pelvic floor muscles cannot increase closing pressure, leakage may occur. Therefore, pressure information used for feedback may be an effective method for controlling the amount of stimulation therapy.

FIG. 4C illustrates an exemplary embodiment of sensor 26C attached to lead 24C. Lead 24C is coupled to sensing device 16 which provides an input signal to operate sensor 26C and receives an output signal from sensor 26C representative of bladder condition. In the example of FIG. 4C, an ultrasound transceiver 46 is exposed on the end of sensor 26. Processing electronics carried by circuit board 32 of sensing device 16 provide an input signal to transceiver 46 which produces ultrasound waves through the urine medium in bladder 14.

Since the waves reflect when encountering a different medium, some ultrasonic energy will be reflected off of the opposite wall of bladder 14. Transceiver 46 receives the reflected waves and produces an output signal which is sent to processing electronics carried by sensing device 16. The output signal is interpreted and processed to detect the distance between transceiver 46 and the opposite bladder wall, given calibration according to the urine medium through which the ultrasound wave is propagated. The distance indicates the size of bladder 14, and hence the amount of stretching of the bladder due to the present urine fill level. In other embodiments, transceiver 46 may produce the ultrasonic waves and a second transducer may detect the reflected waves. In some embodiments, transceiver 46 may include a piezoelectric material which vibrates as current flows through the material. Alternatively, other materials may be used which produce or detect ultrasonic waves.

As bladder 14 fills with urine, the entire bladder will distend to increase the size of the bladder. Therefore, the distance measured by transceiver 46 is indicative of an expanding or contracting bladder. If bladder 14 begins to reduce in size without patient 12 requesting a voiding event, stimulator 18 may increase stimulation to the urinary sphincter or pelvic floor muscles to stop the leaking of urine. Bladder size may also be tracked to monitor patient health and voiding events. If the distance measured by transceiver 46 is not large, indicating that involuntary voiding is not imminent, stimulation parameters may be deactivated or adjusted to conserve power.

Figure 5:
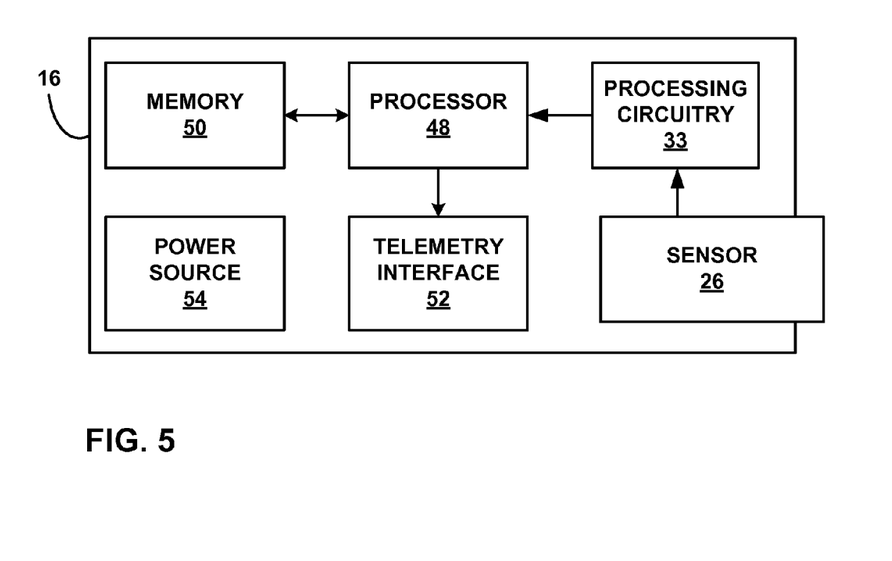
FIG. 5 is functional block diagram illustrating various components of an exemplary implantable sensing device.

FIG. 5 is functional block diagram illustrating various components of an exemplary implantable sensing device. The components described with reference to FIG. 5 are similar to the components described with respect to stimulator 27 from FIG. 2. In the example of FIG. 5, implantable sensing device 16 may include a processor 48, memory 50, telemetry interface 52, power source 54, processing circuitry 55, and sensor 26. Processing circuitry 55 may include appropriate amplifier and filter circuitry for processing of signals generated by sensor 26, and may be provided on a circuit board 32 (FIG. 3) with processor 48, memory 50, and telemetry interface 52. Sensor 26 senses bladder size, fill level, or contraction. In some embodiments, the signals may be converted to digital values and processed by processor 48 before being saved to memory 50 or sent to implantable stimulator 18 or external programmer via telemetry interface 52.

Memory 50 stores instructions for execution by processor 48 and bladder information generated by sensor 26. Bladder information may then be sent to implantable stimulator 18 or external programmer 22 for long-term storage and retrieval by a user. Memory 50 may include separate memories for storing instructions and bladder information. In addition, processor 48 and memory 50 may implement loop recorder functionality in which processor 48 overwrites the oldest contents within the memory with new data as storage limits are met, thereby conserving data storage resources within pressure sensor 16.

Processor 48 controls telemetry interface 52 to send bladder information to implantable stimulator 18 or programmer 22 on a continuous basis, at periodic intervals, or upon request from the implantable stimulator or programmer. Wireless telemetry may be accomplished by radio frequency (RF) communication or proximal inductive interaction of sensing device 16 with programmer 22.

Power source 54 delivers operating power to the components of implantable sensing device 16. Power source 54 may include a battery and a power generation circuit to produce the operating power. As mentioned previously, the battery may be rechargeable to allow extended operation Recharging may be accomplished through proximal inductive interaction between an external charger and an inductive charging coil within sensor 16. In some embodiments, power requirements may be small enough to allow sensor 16 to utilize patient motion and implement a kinetic energy-scavenging device to trickle charge a rechargeable battery. In other embodiments, traditional batteries may be used for a limited period of time. As a further alternative, an external inductive power supply could transcutaneously power sensor 16 whenever pressure measurements are needed or desired.

Figure 6:
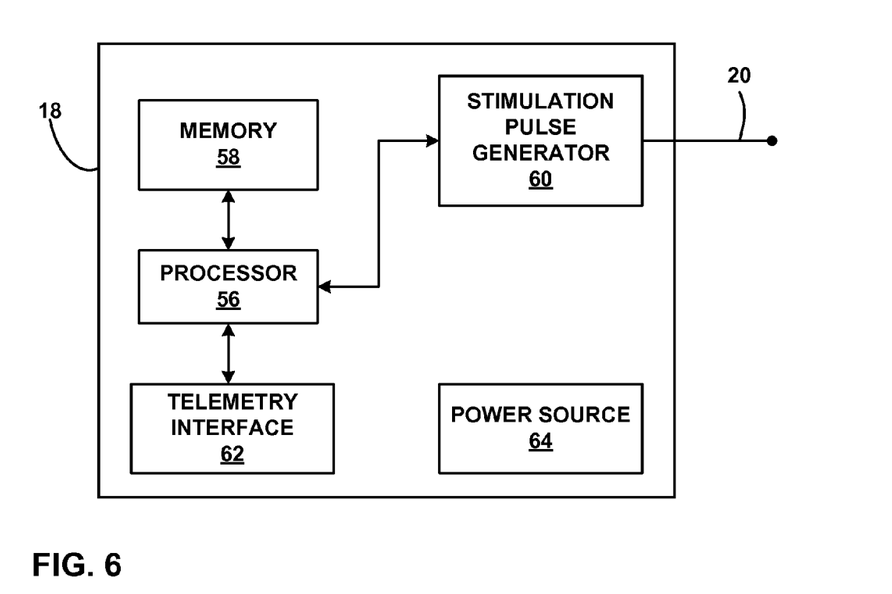
FIG. 6 is a functional block diagram illustrating various components of an implantable stimulator which communicates wirelessly to an implantable sensing device.

FIG. 6 is a functional block diagram illustrating various components of an implantable stimulator 18 that communicates with an implantable sensing device 16. In the example of FIG. 6, stimulator 18 includes a processor 56, memory 58, stimulation pulse generator 60, telemetry interface 62, and power source 64. Memory 58 stores instructions for execution by processor 56, stimulation therapy data, and bladder information received from sensing device 16 via telemetry interface. Bladder information is received from sensing device 16 and may be recorded for long-term storage and retrieval by a user, or adjustment of stimulation parameters, such as amplitude, pulse width or pulse rate. Memory 58 may include separate memories for storing instructions, stimulation parameter sets, and bladder information.

Processor 56 controls stimulation pulse generator 60 to deliver electrical stimulation therapy and telemetry interface 62 to send and receive information. An exemplary range of neurostimulation stimulation pulse parameters likely to be effective in treating incontinence, e.g., when applied to the sacral or pudendal nerves, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts.

3. Pulse Width: between about 10 microseconds and 5000 microseconds, more preferably between approximately 62 microseconds and 620 microseconds, and still more preferably between approximately 180 microseconds and 450 microseconds.

Based on bladder information received from device 16, processor 56 interprets the information and determines whether any therapy parameter adjustments should be made. For example, processor 56 may compare the bladder information to one or more thresholds, and then take action to adjust stimulation parameters based on the bladder information. Information may be received from device 16 on a continuous basis, at periodic intervals, or upon request from stimulator 18 or external programmer 22. Alternatively, or additionally, sensing device 16 may transmit bladder condition information when there is an abrupt change in the bladder activity, e.g., at the onset of involuntary leakage sensed by decreased bladder size or contraction.

Processor 56 modifies parameter values stored in memory 58 in response to bladder information from device 16, either independently or in response to programming changes from external programmer 22. Stimulation pulse generator 60 provides electrical stimulation according to the stored parameter values via a lead 20 implanted proximate to a nerve, such as a sacral nerve. Processor 56 determines any parameter adjustments based on the bladder information obtained from device 16, and loads the adjustments into memory 58 for use in delivery of stimulation.

As an example, if the bladder information indicates a reduction in size of bladder 14 without the approval of patient 12, processor 56 may increase the amplitude, pulse width or pulse rate of the electrical stimulation applied by stimulation pulse generator 60 to increase stimulation intensity, and thereby increase sphincter closing pressure or pelvic floor tone, for example. If bladder size stays constant, processor 56 may implement a cycle of downward adjustments in stimulation intensity until bladder size reduction is evident, and then incrementally increase the stimulation upward until bladder size increases. In this way, processor 56 converges toward an optimum level of stimulation. Although processor 56 is described in this example as adjusting stimulation parameters, it is noted that the adjustments alternatively may be generated by external programmer 22 and transmitted to stimulator 18 as parameter or program changes.

Bladder size or other measurements may change due to a variety of factors, such as an activity type, activity level or posture of the patient 12. Hence, for a given set of stimulation parameters, the efficacy of stimulation may vary in terms of rate of bladder size or pressure, due to changes in the physiological condition of the patient. For this reason, the continuous or periodic availability of bladder condition information from implantable device 16 is highly desirable.

With this bladder information, stimulator 18 is able to respond to changes in bladder activity with dynamic adjustments in the stimulation parameters delivered to patient 12. In particular, processor 56 is able to adjust parameters in order to cause constriction of the urinary sphincter or enhance pelvic floor tone and thereby avoid involuntary leakage. In some cases, the adjustment may be nearly instantaneous, yet prevent leakage. As an example, if patient 12 laughs, coughs, or bends over, the resulting force on bladder 14 could overcome the closing pressure of the urinary sphincter. If sensing device 16 indicates an abrupt change in bladder activity, however, stimulator 18 can quickly respond by more vigorously stimulating the sacral nerves to increase sphincter closing pressure or pelvic floor tone.

In general, if bladder 14 is reducing in size or pressure for an unknown reason, processor 56 may dynamically increase the level of therapy to be delivered to stop the voiding of bladder 14. Conversely, if bladder 14 is increasing in size or pressure consistently, processor 56 may incrementally reduce stimulation, e.g., to conserve power resources, until the bladder reaches a fill stage that correlates with the need to void and, thus, a possible incontinence event. Increases or reductions in the level of therapy may include upward or downward adjustments in amplitude (current or voltage), pulse width, or pulse rate of stimulation pulses delivered to the patient.

As in the case of device 16, wireless telemetry in stimulator 18 may be accomplished by radio frequency (RF) communication or proximal inductive interaction of stimulator 18 with implantable sensing device 16 or external programmer 22. Accordingly, telemetry interface 62 may be similar to telemetry interface 52. Also, power source 64 of stimulator 18 may be constructed somewhat similarly to power source 54. For example, power source 64 may be a rechargeable or non-rechargeable battery, or alternatively take the form of a transcutaneous inductive power interface.

Figure 7:
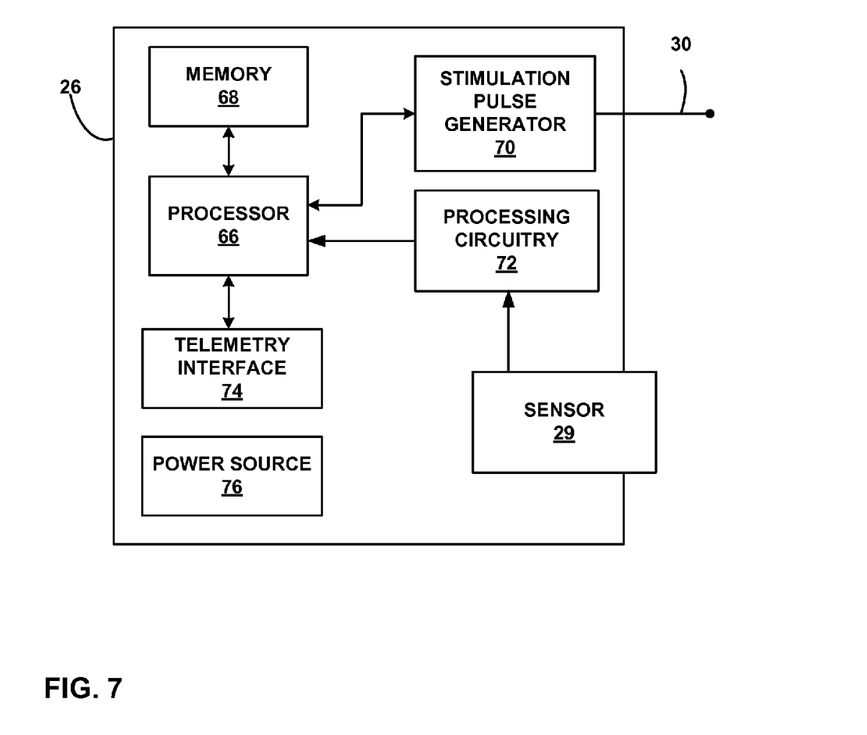
FIG. 7 is a functional block diagram illustrating various components of an implantable stimulator which includes a sensing device.

FIG. 7 is a functional block diagram illustrating various components of an implantable stimulator 27 which includes a sensing device. In the example of FIG. 7, stimulator 27 includes a processor 66, memory 68, stimulation pulse generator 70, telemetry interface 74, and power source 76. In addition, stimulator 26 includes sensor 29 and processing circuitry 72. Essentially, stimulator 26 is a combination of the components of stimulator 18 and sensing device 16. Memory 68 stores instructions for execution by processor 66, stimulation therapy data, and bladder information received from processing circuitry 72. Bladder information received from processing circuitry 72 may be recorded for long-term storage and retrieval by a user, or adjustment of stimulation parameters, such as amplitude, pulse width or pulse rate. Memory 68 may include separate memories for storing instructions, stimulation parameter sets, and bladder information.

Processor 66 controls stimulation pulse generator 60 to deliver electrical stimulation therapy and telemetry interface 74 to send and receive information, and may apply a range of neurostimulation stimulation pulse parameters similar to those identified above with respect to FIG. 6. Based on bladder information received from sensing circuit 72, processor 66 interprets the information and determines whether any therapy parameter adjustments should be made. Processor 66 modifies parameter values stored in memory 68 in response to bladder information from processing circuitry 72, either independently or in response to programming changes from external programmer 22. Stimulation pulse generator 70 provides electrical stimulation according to the stored parameter values via a lead 30 implanted proximate to a nerve, such as a sacral nerve. Processor 66 determines any parameter adjustments based on the bladder information obtained from sensing circuit 72, and loads the adjustments into memory 68 for use in delivery of stimulation.

Figure 8:
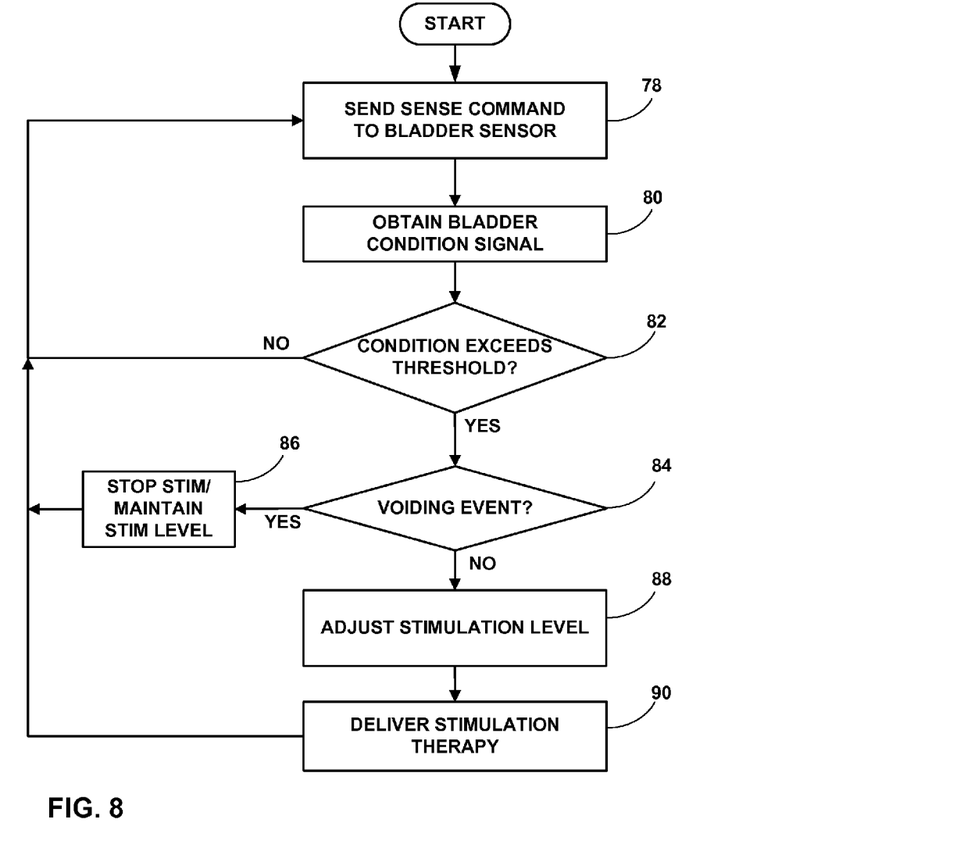
FIG. 8 is a flow chart illustrating a technique for delivery of stimulation therapy based on closed loop feedback from an implantable bladder sensor.

FIG. 8 is a flow chart illustrating a technique for delivery of stimulation therapy based on closed loop feedback from an implantable stimulation system as shown in either FIG. 1 or FIG. 2. The system of FIG. 1 will be used as an example. In the example of FIG. 8, implantable stimulator 18 requires information from implantable sensing device 16 and external programmer 22. The flow of events begins with implantable stimulator 18 communicating with implantable sensing device 16 and sending a command to sense the condition of bladder 14 (78). In other embodiments, sensing device 16 may voluntarily sense a bladder condition on a periodic basis.

Sensing device 16 subsequently acquires a bladder condition measurement and delivers a bladder condition signal to implantable stimulator 18 (80), e.g., by wireless telemetry. Alternatively, the data may be transmitted from sensing device 16 to external programmer 22. Upon receiving the bladder activity signal, implantable stimulator 18 calibrates the data and compares it to a determined threshold (82). If the measured condition does not exceed the applicable threshold value, the loop begins again. If the measured condition exceeds the threshold, the flow continues to the next step of stimulation.

The bladder condition signal may be a signal indicating a level of bladder filling or contraction, or both of bladder 14. The bladder condition signal may be obtained by any of a variety of sensors, such as impedance sensors, pressure sensors, or distance sensors, as described herein. If sensor 16 includes a strain gauge sensor, the bladder condition signal may be based on a change in impedance of the strain gauge or a voltage across the strain gauge that varies as a function of the impedance change. The impedance of the strain gauge changes in response to deflection of the strain gauge in the presence of bladder pressure. The bladder condition signal may be based on a single sample, or a series of samples over a period of time. Hence, the bladder condition signal may indicate an instantaneous amplitude or a rate of change, i.e., slope, in amplitude over a series of samples, or a combination thereof.

As a further alternative, more sophisticated digital signal processing may be used to correlate a series of samples with a waveform or pattern known to be indicative of contraction. The processing of the measurements obtained by a sensing element may be performed by processing electronics and/or software provided onboard with sensor 16, or by processing electronics and/or software provided by stimulator 18 or external programmer 22. Hence, stimulator 18 or external programmer 22 may receive raw sense data from sensor 16, or pre-processed bladder activity signals from sensor 16. In addition, the threshold comparison represented by reference numeral 82 may be performed within stimulator 18 or external programmer 22, or within sensor 18 itself in some embodiments.

Stimulator 18 and programmer 22 may receive sense data from sensor 16 in some embodiments. For example, stimulator 18 may react to instantaneous changes in bladder condition, while programmer 22 may react to changes in bladder condition over a period of time, e.g., trend data. Alternatively, either stimulator 18 or programmer 22 may be configured to react to instantaneous and trending bladder changes.

In some embodiments, implantable stimulator 18 may communicate with external programmer 22 to check if patient 12 has desired to void the contents of bladder 14 (80). If a bladder condition signal such as a contraction or fill level exceeds an applicable threshold (82), but patient 12 has signaled a voiding event (84), e.g., via external programmer 22, stimulation may be stopped for a brief window of time or maintained at its current stimulation level to enable the patient to urinate (86). Stimulation then begins again and bladder sensing starts once more. In the case in which no voiding event desired, the urinary sphincter or pelvic floor muscles may need to be stimulated to counteract bladder contraction. Implantable stimulator 18 performs the necessary tasks to adjust the level of stimulation (88), including adjustment of amplitude, pulse width or rate, or electrode combination and polarity, and thereby increases closing bladder force. Stimulator 18 concludes the loop by delivering stimulation therapy to appropriate nerves, such as the nerves that innervate the sphincter or pelvic floor muscles (90). After voiding, stimulation may be turned off until bladder 14 reaches a particular fill stage. After stimulation therapy has commenced, the loop restarts to continue appropriate incontinence therapy to patient 12.

Figure 9:
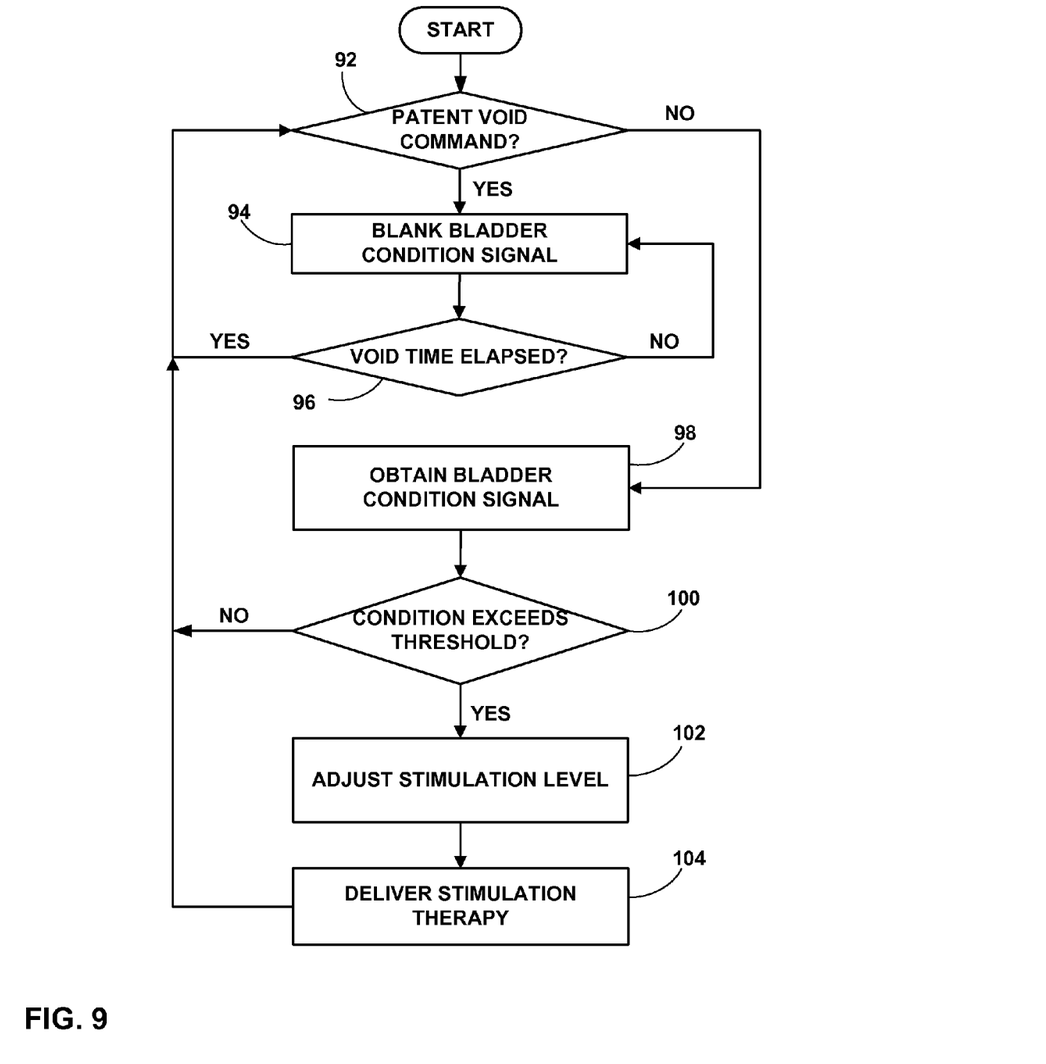
FIG. 9 is a flow chart illustrating an alternative technique for delivery of stimulation therapy based on closed loop feedback from an implantable bladder sensor.

FIG. 9 is a flow chart illustrating an alternative technique for delivery of stimulation therapy based on closed loop feedback from an implantable bladder sensor. In some cases, stimulation may be delivered at a level that prevents unintentional voiding of urine, but permits the patient to intentionally overcome the stimulation to void urine. Accordingly, stimulation does not necessarily need to be stopped for intentional voiding. However, it is desirable that the stimulation level not be increased in response to bladder contraction or a bladder fill stage while the patient is attempting to void urine. For this reason, it may be desirable to apply a blanking interval to sensing device 16. The blanking interval is a period during which sensing device 16 does not sense bladder activity, or any sensed activity is ignored, so that stimulation is not inadvertently adjusted in response to bladder contraction associated with an intentional voiding event.

As shown in FIG. 9, if a patient void command is received (92), e.g., by user input to an external programmer 22, the programmer 22 applies a blanking interval to the bladder condition signal (94). The blanking interval may be a period during which bladder condition signals produced by sensing device 16 are ignored by programmer 22, stimulator 18, or both. Alternatively, during the blanking interval, programmer 22 or stimulator 18 may send a wireless command to actively disable sensor 16 temporarily. Programmer 22 may directly blank sensing device 16 or blank the sensing device via stimulator 18. The blanking interval may extend for a predetermined period of time known to be sufficient to complete voiding. Once the voiding time has elapsed (96), programmer 22 may again determine whether a patient void command has been entered (92). Another patient void command resets the blanking interval.

If no patient void command has been received (92), sensing device 16 obtains the bladder condition signal (98) and provides the signal to programmer 22 or stimulator 18. The bladder condition signal may be provided on a periodic or polled basis. If the condition, such as fill stage or contraction force, exceeds an applicable threshold (100), such as a size or pressure threshold, programmer 22 or stimulator 18 adjusts the stimulation level (102), e.g., by adjusting one of more stimulation pulse parameters such as amplitude, pulse width or pulse rate, or electrode combination or polarity. The level is adjusted to a level sufficient to avoid involuntary voiding, i.e., an incontinence event. Upon delivery of the stimulation therapy with the adjusted stimulation level (104), the process continues. In particular, programmer 22 may react to a patient void command (92) at any time.

In some embodiments, bladder sensor 16 may be used exclusively for monitoring bladder activity without providing feedback for stimulation therapy. In this case, the process represented in FIG. 8 would be much simpler and only include collecting data and sending it to external programmer 22. Bladder conditions may be measured continuously, intermittently or at the request of stimulator 18 or external programmer 22. These embodiments may be used for disease diagnosis or condition monitoring and may enable patient 12 to avoid frequent clinic visits and uncomfortable procedures. In some embodiments, the bladder measurements may form part of an automated voiding diary that records voluntary voiding events, involuntary voiding events, and bladder activity levels prior to, contemporaneous with, of after such an event.

Various embodiments of the described invention may include processors that are realized by microprocessors, Application-Specific Integrated Circuits (ASIC), Field-Programmable Gate Arrays (FPGA), or other equivalent integrated or discrete logic circuitry. The processor may also utilize several different types of data storage media to store computer-readable instructions for device operation. These memory and storage media types may include any form of computer-readable media such as magnetic or optical tape or disks, solid state volatile or non-volatile memory, including random access memory (RAM), read only memory (ROM), electronically programmable memory (EPROM or EEPROM), or flash memory. Each storage option may be chosen depending on the embodiment of the invention.

Many embodiments of the invention have been described. Various modifications may be made without departing from the scope of the claims. For example, although the invention has been generally described in conjunction with implantable neurostimulation devices, a sensing device may also be used with other implantable medical devices, such as electrical muscle stimulation devices, functional electrical stimulation (FES) devices, and implantable drug delivery devices, each of which may be configured to treat incontinence or other conditions or disorders. These and other embodiments are within the scope of the following claims.

The invention claimed is:

1. A method comprising:
    sensing a condition within an interior of a bladder from a position within the interior of the bladder via a sensor carried on a distal end of a lead and positioned within the interior of the bladder, the lead having an electrical conductor therein and extending, via penetration of a wall of the bladder, from the interior of the bladder to a sensing device implanted outside of the bladder;

generating, via a processor within the sensing device, information based on the bladder condition within the interior of the bladder sensed by the sensor from the position within the interior of the bladder; and delivering, via an implantable stimulator, electrical stimulation therapy based on the information.

2. The method of claim 1, wherein delivering electrical stimulation therapy comprises delivering electrical stimulation therapy for urinary incontinence based on the information.

3. The method of claim 1, wherein the sensed bladder condition includes at least one of a bladder size or bladder pressure.

4. The method of claim 1, wherein the sensed bladder condition includes at least one of a bladder fill level or bladder contraction.

5. The method of claim 1, further comprising transmitting the sensed bladder condition to an external programmer that is configured to control the implantable stimulator to deliver electrical stimulation therapy for urinary incontinence based on the information.

6. The method of claim 1, further comprising detecting, via the sensor, impedance within the interior of the bladder, wherein the impedance is indicative of a bladder fill level, and wherein generating information based on the bladder condition comprises generating information based on the detected impedance.

7. The method of claim 1, wherein the sensing device is attached to an exterior surface of the bladder.

8. The method of claim 1, wherein the sensing device includes a power supply.

9. The method of claim 1, wherein the sensor includes at least one of an impedance sensor, an ultrasonic sensor, or a pressure sensor.

10. An implantable electrical stimulation system comprising:

a sensing device adapted to be implanted outside of a bladder;

a lead having an electrical conductor therein and adapted to extend from the sensing device into an interior of the bladder via penetration of a wall of the bladder;

a sensor, adapted to be carried at a distal end of the lead and positioned within the interior of the bladder, wherein the sensor is configured to sense a condition within the interior of the bladder from the position within the interior of the bladder;

a processor within the sensing device, wherein the processor is configured to generate information based on the bladder condition within the interior of the bladder sensed by the sensor from the position within the interior of the bladder; and an implantable stimulator that delivers electrical stimulation therapy based on the information.

11. The system of claim 10, further comprising an external programmer configured to control the delivery of the stimulation therapy in response to the information.

12. The system of claim 10, wherein the sensed bladder condition includes at least one of a bladder size or bladder pressure.

13. The system of claim 10, wherein the sensed bladder condition includes at least one of a bladder fill level or bladder contraction.

14. The system of claim 10, wherein the sensor includes at least one of an impedance sensor, an ultrasonic sensor, or a pressure sensor.

15. The system of claim 10, wherein the sensing device includes a power supply.

16. The system of claim 10, further comprising a fixation structure to attach the sensing device to an exterior surface of the bladder.

17. The system of claim 10, wherein the implantable stimulator configures the electrical stimulation therapy to alleviate urinary incontinence.

18. The system of claim 10, wherein the sensor comprises an impedance sensor adapted to be positioned within the interior of the bladder, wherein the impedance sensor is configured to detect impedance within the bladder, wherein the impedance is indicative of a bladder fill level, and wherein the processor is configured to generate the information by at least generating the information based on the detected impedance.

* * * * *